United States Patent
Shin et al.

(10) Patent No.: US 10,813,622 B2
(45) Date of Patent: Oct. 27, 2020

(54) ULTRASONIC DIAGNOSTIC APPARATUS AND CONTROL METHOD THEREOF

(71) Applicant: SAMSUNG MEDISON CO., LTD., Gangwon-do (KR)

(72) Inventors: Cheon Seop Shin, Seoul (KR); Kyeong Gu Woo, Suwon-si (KR); Sung Won Lim, Paju-si (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 1351 days.

(21) Appl. No.: 14/664,761

(22) Filed: Mar. 20, 2015

(65) Prior Publication Data
US 2016/0066884 A1 Mar. 10, 2016

(30) Foreign Application Priority Data
Sep. 5, 2014 (KR) .................. 10-2014-0118835

(51) Int. Cl.
*A61B 8/00* (2006.01)

(52) U.S. Cl.
CPC .............. *A61B 8/4405* (2013.01); *A61B 8/54* (2013.01); *A61B 8/461* (2013.01)

(58) Field of Classification Search
CPC . A61B 8/4405; A61B 8/54; A61B 8/461–462; B62B 3/02–10
See application file for complete search history.

(56) References Cited

U.S. PATENT DOCUMENTS

| 6,012,693 | A   | * | 1/2000  | Voeller | F16M 11/048 248/279.1 |
| 6,296,216 | B1  | * | 10/2001 | Law     | A47B 17/033 248/278.1 |
| 6,478,275 | B1  |   | 11/2002 | Huang   |                       |
| 7,013,813 | B2  | * | 3/2006  | Lima    | A47B 21/0314 108/10   |

(Continued)

FOREIGN PATENT DOCUMENTS

| CN | 204106040 U | 1/2015  |
| DE | 3312137 A1  | 10/1984 |

(Continued)

OTHER PUBLICATIONS

Extended European Search Report dated Jul. 24, 2015 issued in European Patent Application No. 15153527.5.
(Continued)

*Primary Examiner* — Theodore J Stigell
*Assistant Examiner* — Sean A Frith
(74) *Attorney, Agent, or Firm* — Morgan, Lewis & Bockius LLP

(57) ABSTRACT

Disclosed herein are an ultrasonic diagnostic apparatus having a movement unit movably connected to a body, and a control method thereof. The ultrasonic diagnostic apparatus includes a body, a movement unit movably connected at the body, at least one connecting unit having a first end unit rotatably coupled to the body and a second end unit rotatably coupled to the movement unit, and at least one rail installed at least at the one of the body or the movement unit such that at least the one of the first end unit or the second end unit may be slidingly moved. The movement unit may be conveniently moved to a desired position by a user.

12 Claims, 18 Drawing Sheets

(56) References Cited

U.S. PATENT DOCUMENTS

| | | | |
|---|---|---|---|
| 7,222,826 B1* | 5/2007 | Berglund | A47B 21/0314 248/118 |
| 7,562,852 B2* | 7/2009 | Wang | A47B 21/0314 108/140 |
| 8,864,091 B1* | 10/2014 | Patriarco | A47B 21/0314 108/143 |
| 9,451,931 B2* | 9/2016 | Ninomiya | B62B 3/02 |
| 2003/0025054 A1 | 2/2003 | Toennesland et al. | |
| 2005/0205734 A1 | 9/2005 | Wang | |
| 2007/0010745 A1 | 1/2007 | Foot et al. | |
| 2009/0212678 A1* | 8/2009 | Sung | A47B 77/18 312/333 |
| 2009/0301360 A1* | 12/2009 | Copeland | G06F 3/021 108/68 |
| 2010/0094130 A1* | 4/2010 | Ninomiya | A61B 8/462 600/437 |
| 2011/0224544 A1* | 9/2011 | Ahn | A61B 8/46 600/437 |
| 2011/0247532 A1* | 10/2011 | Jones | A47B 9/02 108/147 |
| 2012/0235000 A1 | 9/2012 | Borloz et al. | |
| 2013/0030292 A1* | 1/2013 | Nakajima | A61B 8/463 600/437 |
| 2016/0120507 A1* | 5/2016 | Ninomiya | G06F 3/03 345/1.3 |

FOREIGN PATENT DOCUMENTS

| | | |
|---|---|---|
| JP | 2005-342056 A | 12/2005 |
| KR | 2009-0070584 A | 7/2009 |
| WO | 2013/15826 A1 | 1/2013 |

OTHER PUBLICATIONS

Office Action issued in corresponding European Application No. 15 153 527.5, dated May 10, 2019.

* cited by examiner (a)

(b)

(c)

(d)

(a)

(b)

(c)

(d)

(a)

(b)

(c)

(d)

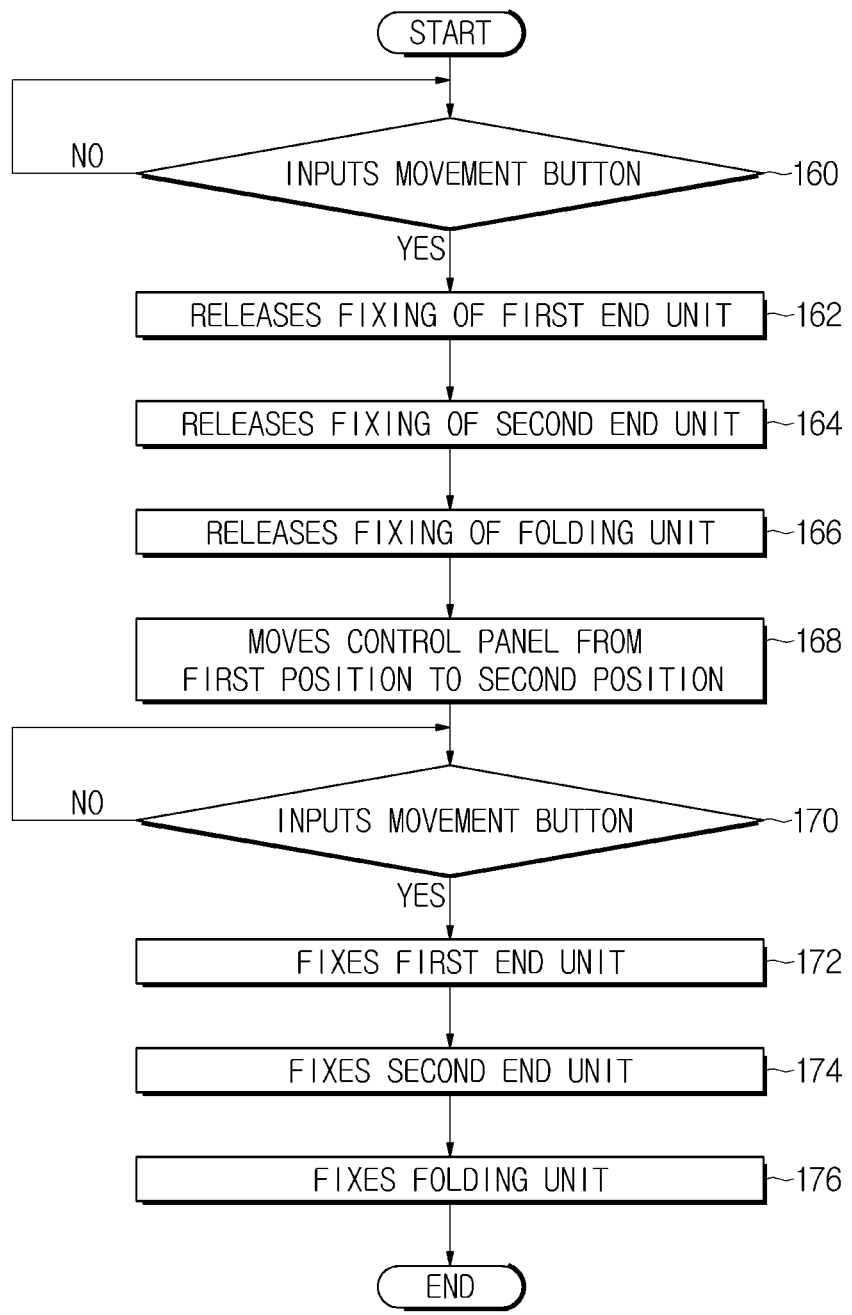

ULTRASONIC DIAGNOSTIC APPARATUS AND CONTROL METHOD THEREOF

CROSS-REFERENCE TO RELATED APPLICATION

This application claims the benefit of the Korean Patent Application No. 10-2014-0118835, filed on Sep. 5, 2014, in the Korean Intellectual Property Office, the disclosure of which is incorporated herein by reference.

BACKGROUND

1. Field

Embodiments of the present disclosure relate to an ultrasonic diagnostic apparatus and a control method thereof, and more particularly, an ultrasonic diagnostic apparatus having a movement unit movably connected to a body and a control method thereof.

2. Description of the Related Art

An ultrasonic diagnostic apparatus is an apparatus configured to radiate ultrasonic signals from a surface of a subject toward a diagnostic portion at an inside a body of the subject, and then obtain an image related to cross sectional layers or blood flow of a tissue by use of the information from the ultrasonic signals that is reflected. The apparatus as such is provided in smaller size and at lower cost when compared to other imaging apparatuses such as an x-ray imaging apparatus, a CT Scanner (Computerized Tomography Scanner), an MRI (Magnetic Resonance Image), and a nuclear medicine diagnostic apparatus. In addition, the apparatus as such is capable of displaying in real time, and, as with the x-ray imaging apparatus, is provided with high level of safety as no radiation exposure is present, and thus is widely used in diagnoses of hearts, abdomens, reproductive organs, and obstetrics.

The ultrasonic diagnostic apparatus as such includes a probe configured to radiate ultrasonic signals, and receive the ultrasonic signals, that is, ultrasonic echo signals, that are reflected. In addition, ultrasonic diagnostic apparatus as such includes a body configured to control the ultrasonic signals being radiated through the probe or generate needed images by use of the ultrasonic signals being received, and a control panel connected to the body and capable of having the ultrasonic diagnostic apparatus manipulated by a user.

The user is provided to manipulate the control panel in a state of the probe being in contact with respect to a subject, and the control panel is needed to be moved to a convenient position for the user to manipulate. At this time, moving the body that is bulky may not be convenient, and thus a structure capable of independently move the control panel away from the body according to needs of the user is needed.

SUMMARY

Therefore, it is an aspect of the present disclosure to provide an ultrasonic diagnostic apparatus having a movement unit movably installed according to needs of a user.

It is another aspect of the present disclosure to provide an ultrasonic diagnostic apparatus configured such that the movement unit may be moved to a desired position by a user and capable of fixing the movement unit.

Additional aspects of the disclosure will be set forth in part in the description which follows and, in part, will be obvious from the description, or may be learned by practice of the disclosure.

In accordance with one aspect of the present disclosure, an ultrasonic diagnostic apparatus includes a body, a movement unit, at least one connecting unit, and at least one rail. The movement unit may be movably connected to the body. The at least one connecting unit may have a first end unit rotatably coupled to the body and a second end unit rotatably coupled to the movement unit. The at least one rail may be installed on at least one of the body and the movement unit such that at least one of the first end unit and the second end unit is slidingly moved.

The at least one rail may be installed on one surface of the movement unit such that the second end unit is moved along one surface of the body.

The second end unit may be rotatably coupled to a lower surface of the movement unit, and the at least one rail may be installed at a lower surface of the movement unit.

The at least one rail may be recessively formed at a lower surface of the movement unit.

The at least one rail may include a body rail installed at the body, and a movement unit rail installed at the movement unit.

As for the first end unit to be moved along one surface of the body, the body rail may be installed at the one surface of the body, and as for the second end unit to be moved along one surface of the movement unit, the movement unit rail may be installed at the one surface of the movement unit.

The at least one connecting unit may include a first connecting member and a second connecting member connecting the body and the movement unit, respectively.

The at least one rail may include a first rail installed at the movement unit such that the second end unit of the first connecting member is slidingly moved, and a second rail installed at the movement unit such that the second end unit of the second connecting member is slidingly moved.

The first rail and the second rail may be installed on one surface of the movement unit while spaced apart from each other.

The at least one connecting unit may include at least one folding unit disposed in between the first end unit and the second end unit.

The at least one folding unit may be installed such that the second end unit is vertically moved with respect to the first end unit.

The at least one connecting unit may include a fixing member configured to fix the first end unit and the second end unit at predetermined positions.

In accordance with one aspect of the present disclosure, a method of controlling an ultrasonic diagnostic apparatus having a connecting unit provided with a first end unit and a second end unit includes releasing a fixing of the first end unit coupled to the body to be rotated, releasing a fixing of the second end unit coupled to the movement unit to be rotated, releasing a fixing of the second end unit to be moved along a rail provided at the movement unit, fixing a moving of the second end unit disposed at a predetermined position at an inside the rail according to the movement unit that is moved from a first position to a second position, fixing the second end unit to be prevented from rotating, and fixing the first end unit to be prevented from rotating.

The first end unit and the second end unit each may be released from being fixed as to be rotated at a predetermined angle, and the second end unit may be released from being fixed as to be moved to a predetermined position along the rail, so that the movement unit is moved from the first position to the second position in the least distance.

The first position and the second position may be random positions on a x-y plane surface.

A folding unit disposed in between the first end unit and the second end unit may be released from being fixed as to be moved, and a moving of the folding unit disposed at a predetermined position according to the movement unit that is moved from the first position to the second position may be fixed.

The first position and the second position may be random positions on a x-y-z space.

BRIEF DESCRIPTION OF THE DRAWINGS

These and/or other aspects of the disclosure will become apparent and more readily appreciated from the following description of the embodiments, taken in conjunction with the accompanying drawings of which:

FIG. 18 is a drawing illustrating a control method of the ultrasonic diagnostic apparatus in accordance with one embodiment of the present disclosure.

DETAILED DESCRIPTION

Figure 1:
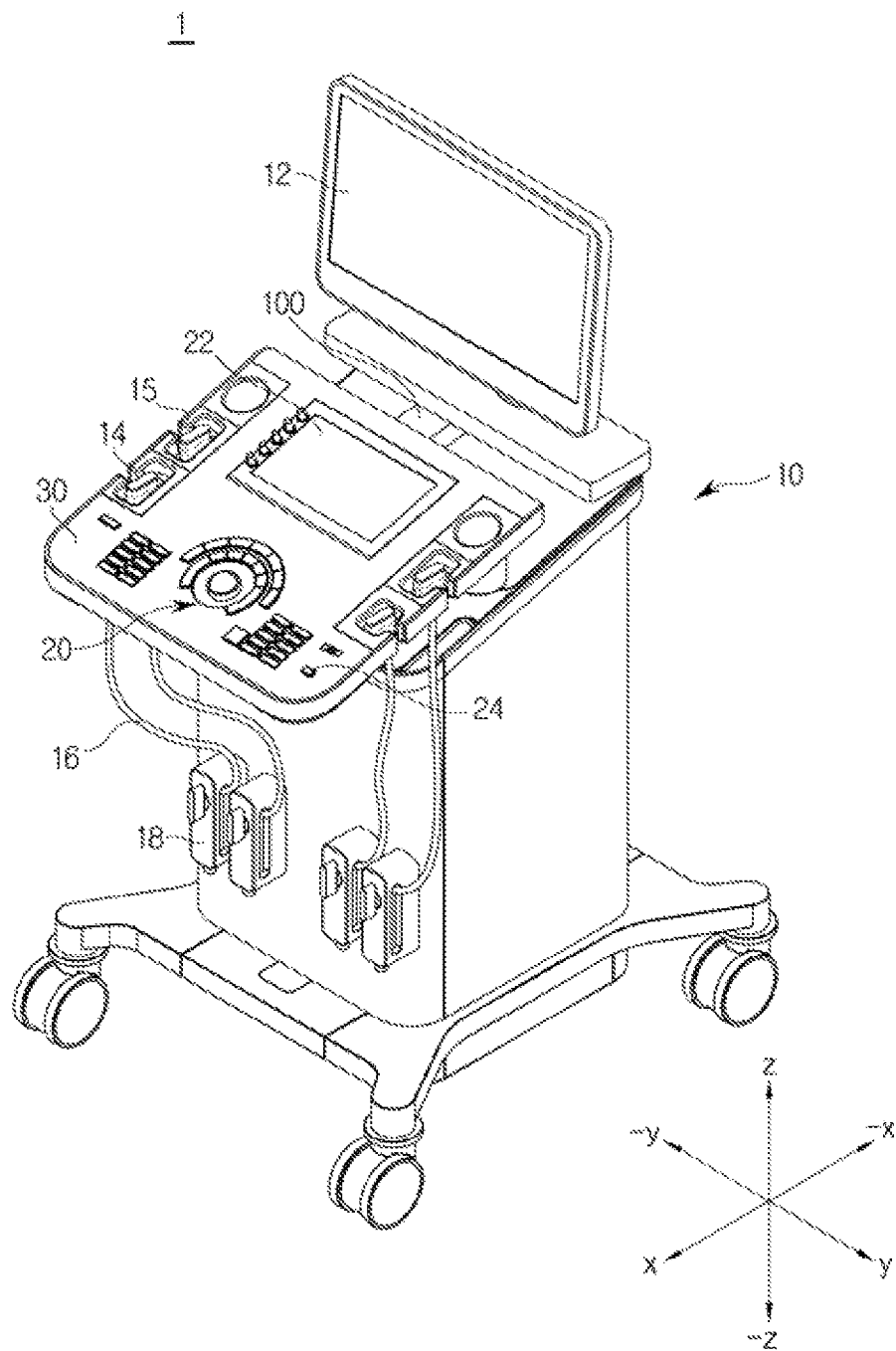
FIG. 1 and FIG. 2 are drawings illustrating an ultrasonic diagnostic apparatus in accordance with one embodiment of the present disclosure.

Reference will now be made in detail to the embodiments of the present disclosure, examples of which are illustrated in the accompanying drawings, wherein like reference numerals refer to like elements throughout.

Figure 2:
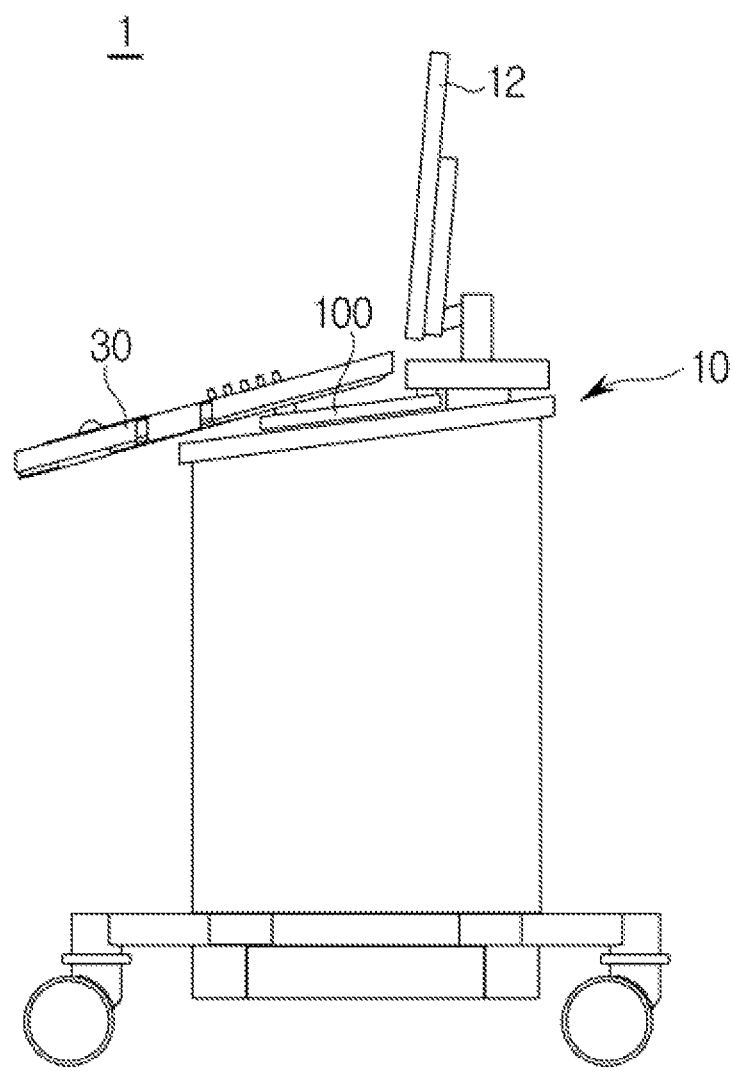

FIG. 1 and FIG. 2 are drawings illustrating an ultrasonic diagnostic apparatus in accordance with one embodiment of the present disclosure. An ultrasonic diagnostic apparatus 1 may include a body 10, a display 12 disposed at the body 10, a probe 14, and a control panel 30.

The display 12 and the control panel 30 may be movably connected to one side of the body 10. In addition, apparatuses needed for the ultrasonic diagnostic apparatus 1 other than the display 12 and the control panel 30 may be movably connected to the body 10. The apparatuses movably connected to the body 10 as such are referred to as movement units. The movement units as such will be described later.

Various parts such as a CPU (Central Processing Unit), a MCU (Micro Control Unit), and image processing apparatus configured to perform the controlling of sending ultrasonic signals and the processing of received ultrasonic signals may be provided at the body 10.

The display 12 is installed at an upper portion of the body 10 and capable of displaying results of ultrasonic diagnoses via images. As illustrated on FIG. 1, the display 12 may be installed at the body 10 or at the control panel 30.

The display 12 is capable of displaying ultrasonic images according to a display mode that is preset or set by a user. The display mode includes an A-mode (Amplitude mode), a B-mode (Brightness mode), a D-mode (Doppler Mode), an E-mode (Elastography mode), and a M-mode (Motion mode).

The display 12 may be implemented by use of a Liquid Crystal Display (LCD), a Light Emitting Diode (LED), an Organic Light Emitting Diode (OLED), a Plasma Display Panel (PDP), and a Cathode-Ray Tube (CRT).

The probe 14 may include a plurality of transducers. The transducer is configured to send ultrasonic signals to a subject after reciprocally converting the ultrasonic signals and electrical signals, and receive ultrasonic echo signals being reflected from the subject.

The transducer may be one of a Magnetostrictive Ultrasound Transducer configured to use magnetostrictive effect of a magnetic substance according to a method of reciprocally converting ultrasonic signals and electric signals, a capacitive micromachined Ultrasonic Transducer (cMUT) configured to send/receive ultrasonic signals by use of vibrations of micro-processed hundreds or thousands of thin films, and a Piezo-electric Ultrasonic Transducer configured to use a piezoelectric effect of piezoelectric substance.

The probe 14 may be connected to the body 10 through a cable 16. The probe 14 is connected to one end of the cable 16, and a male connector 18 may be connected to the other end of the cable 16. As the male connector 18 is physically coupled to a female connector (not shown) provided at the body 10, the probe 14 and the body 10 may be connected to each other.

On FIG. 1, the male connector 18 and the cable 16 are illustrated to be exposed to an outside, but the male connector 18 and the cable 16 may be provided at a housing forming the body 10. In addition, on FIG. 1, a probe holder 15 provided to dispense the probe 14 is illustrated to be provided at a control panel 30, but the probe holder 15 may be provided at the body 10 according to the convenience of a user. In addition, the probe holder 15 may be provided at the both of the body 10 and the control panel 30.

The control panel 30 may be manipulated by a user as to control the ultrasonic diagnostic apparatus 1. An input apparatus 20 and an auxiliary display 22 may be provided at the control panel 30. The input apparatus 20 may include various buttons having a movement button 24, a knob, a trackball, and a joy stick. The auxiliary display 22 is capable of providing menu to optimize ultrasonic images or information such as auxiliary images, or a graphic interface to a user.

The auxiliary display 22, similar to the display 12, may be implemented by use of a Liquid Crystal Display (LCD), a Light Emitting Diode (LED), an Organic Light Emitting Diode (OLED), a Plasma Display Panel (PDP), and a Cathode-Ray Tube (CRT). In addition, the auxiliary display 22 may be implemented in the form of a touch screen by further having a touch panel.

As described above, the ultrasonic diagnostic apparatus 1 may include a movement unit movably connected to one side of the body 10. A user is needed to perform scans for a long period of time while positioned next to a patient as to perform an ultrasonic diagnosis, and various apparatuses including the moving apparatus are needed to be manipulated while performing the scans. Thus, the ultrasonic diagnostic apparatus 1 is configured to provide a structure capable of freely moving according to intentions of a user as to enhance convenience of the user in a state when the movement unit is connected to the body 10.

In particular, a user may be able to move mainly the control panel 30 configured to control motions of the ultrasonic diagnostic apparatus 1. Hereinafter, one embodiment of the present disclosure will be described by using the control panel 30 of the movement unit as one example.

Thus, the ultrasonic diagnostic apparatus 1 may include a connecting unit 100 configured to movably connect the control panel 30 to the body 10.

In the embodiment, while having the position of the body 10 as a center, a x-axis direction is referred to as a forward direction, a—x-axis direction is referred to as a backward direction, a—y-axis direction is referred to as a left side, a y-axis direction is referred to as a right side, a z-axis direction is referred to as an upper direction, and a 1 z-axis direction is referred to as a lower direction. However, as illustrated on FIG. 1 and FIG. 2, the control panel 30 is installed at the body 10 at a predetermined angle. Hereinafter, the x-axis and the—x-axis are referred to as directions to which the control panel 30 is forwardly/backwardly moved with respect to the body 10.

Hereinafter, along with a structure of the connecting unit 100 configured to connect the control panel 30 and the body 10, motions of the control panel 30, which are provided to be available through the structure as such, will be described in detail.

Figure 3:
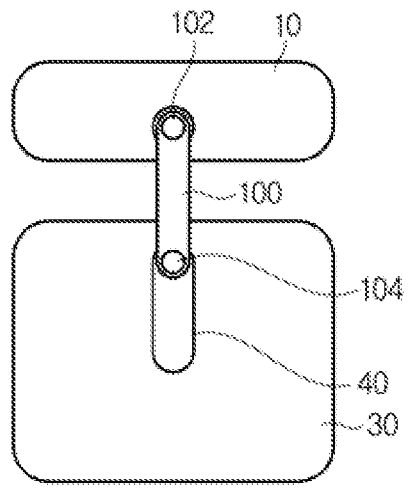
FIG. 3 is a drawing illustrating a operation status of a control panel of the ultrasonic diagnostic apparatus in accordance with one embodiment of the present disclosure.
Figure 3:
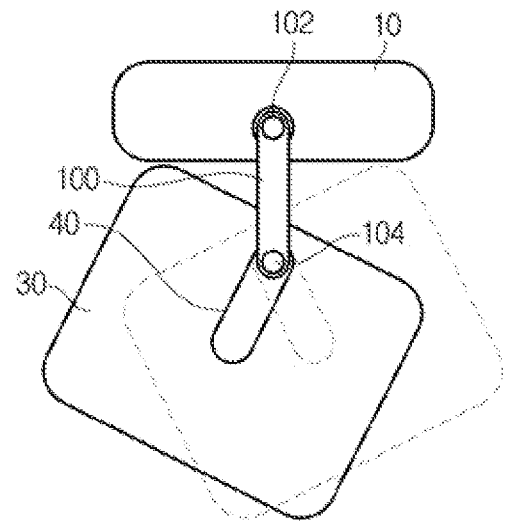
Figure 3:
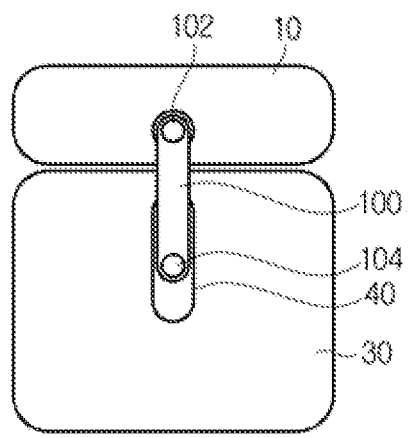
Figure 3:
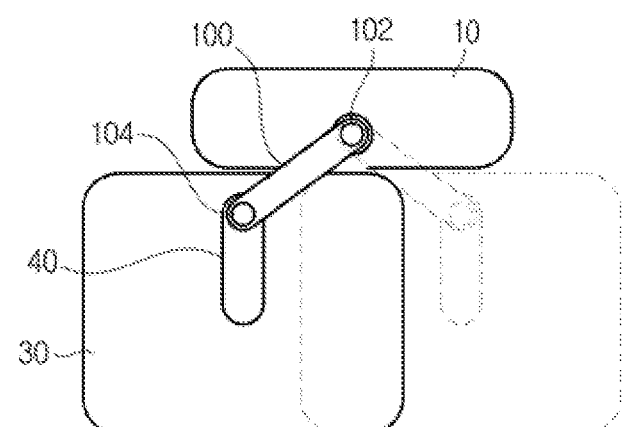

FIG. 3 is a drawing illustrating a operation status of the control panel of the ultrasonic diagnostic apparatus in accordance with one embodiment of the present disclosure.

The connecting unit 100 may include a first end unit 102 coupled to the body 10 and a second end unit 104 coupled to the control panel 30. At least one of the connecting unit 100 may be provided in between the body 10 and the control panel 30. The first end unit 102 and the second end unit 104 may be rotatably coupled to the body 10 and the control panel 30, respectively.

The at least one of the body 10 and the control panel 30 may include at least one rail 40. The rail 40 may be integrally formed at the body 10 and the control panel 30. The at least one of the first end unit 102 and the second end unit 104 may be slidingly moved along the rail 40.

In accordance with an embodiment of the present disclosure, the first end unit 102 and the second end unit 104 may be coupled to lower surfaces of the body 10 and the control panel 30, respectively, but are not limited hereto, and the first end unit 102 and the second end unit 104 may be coupled to random positions of the body 10 and the control panel 30. In addition, the rail 40 may be installed at one surface at which the first end unit 102 and the second end unit 104 are positioned.

Hereinafter, FIGS. 3 to 16 are schematically illustrated drawings as to illustrate shapes and movements of various connecting units.

FIG. 3 is provided to illustrate lower surfaces of the body 10 and the control panel 30 as to illustrate the first end unit 102, the second end unit 104, and the rail 40. On FIG. 3, the connecting unit 100 is provided with one unit thereof in between the body 10 and the control panel 30, and the rail 40 is provided at the control panel 30.

As illustrated on FIG. 3, the first end unit 102 is coupled to a lower surface of the body 10, and the second end unit 104 is coupled to a lower portion of the control panel 30. In addition, as for the second end unit 104 to be moved along a lower surface of the control panel 30, the rail 40 is installed at a lower surface of the control panel 30.

As shown on FIG. 3 (*b*), the control panel 30 may be rotated at a predetermined angle as the second end unit 104 is rotatably installed at the control panel 30. In addition, the second end unit 104 is movably installed along the rail 40, and thus may be able to move toward the forward/backward directions, that is, the x-axis direction and the—x-axis direction. As shown on FIG. 3 (*b*), the control panel 30 may be moved toward the left/right sides, that is, the y-axis direction and the—y-axis direction as the first end unit 102 as well is rotatably installed at the body 10.

As the above, the control panel 30 may be moved from a first position to a second position according to needs of a user. The movements of FIG. 3 (*a*), (*b*), and (*c*) are overlappingly taken place, and the control panel 30 may be moved to a random position or rotated at a random position on an x-y plane surface. The first position and the second position are referred to as the random positions on the x-y plane surface, and the control panel 30 may be moved form the first place to the second place in the least distance.

Figure 4:
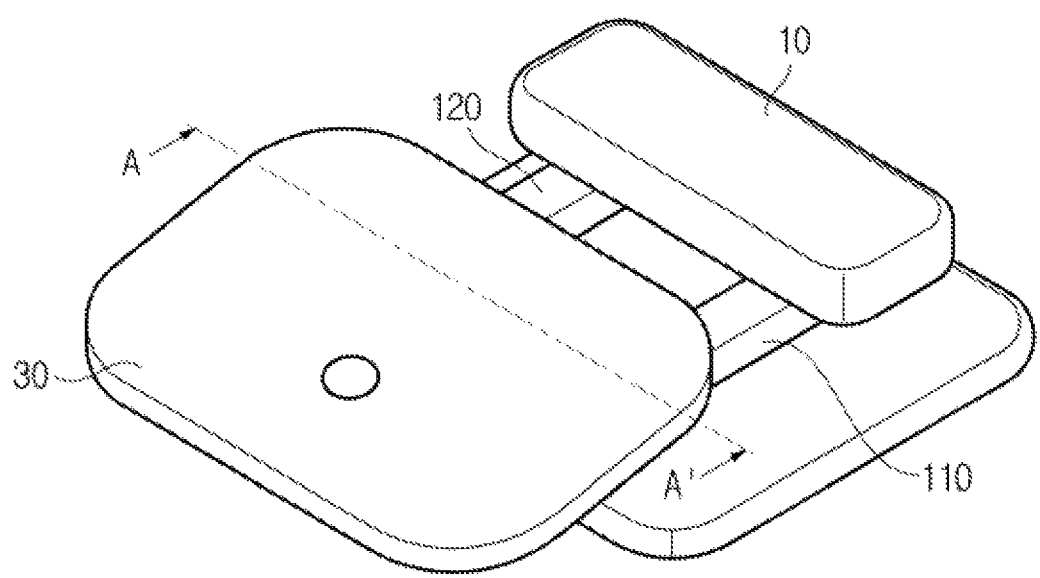
FIG. 4 is a drawing illustrating a control panel of an ultrasonic diagnostic apparatus in accordance with another embodiment of the present disclosure.

FIG. 4 is a drawing illustrating a control panel of an ultrasonic diagnostic apparatus in accordance with another embodiment of the present disclosure. FIG. 4 is illustrated after deleting structures that are not needed, as to illustrate a shape of the body and the control panel being connected with respect to each other.

The connecting unit 100 may be provided in a plurality of units as to stably connect the body 10 and the control panel 30. As illustrated on FIG. 4, the connecting unit 100 includes a first connecting member 110 and a second connecting member 120 to connect the body 10 and the control panel 30, respectively.

The first connecting member 110 and the second connecting member 120 includes first end units 112 and 122 and second end units 114 and 124, respectively. In addition, the rail 40 includes a first rail 42 and a second rail 44 as to slidingly move the second end unit 114 of the first connecting member 110 and the second end unit 124 of the second connecting member 120, respectively.

The first rail 42 and the second rail 44 may be installed at one surface of the control panel 30 while spaced apart from each other. As illustrated on FIGS. 5 to 7, the first rail 42 and the second rail 44 may be parallelly disposed at a lower surface of the control panel 30. In addition, as illustrated on FIG. 8, the first rail 42 and the second rail 44 each may be disposed at a lower surface of the control panel 30 while provided with a predetermined angle.

Hereinafter, FIGS. 5 to 8 is provided to illustrate the lower panels of the body and the control panel as to illustrate motions of the control panel that is provided by use of the first connecting member and the second connecting member.

Figure 5:
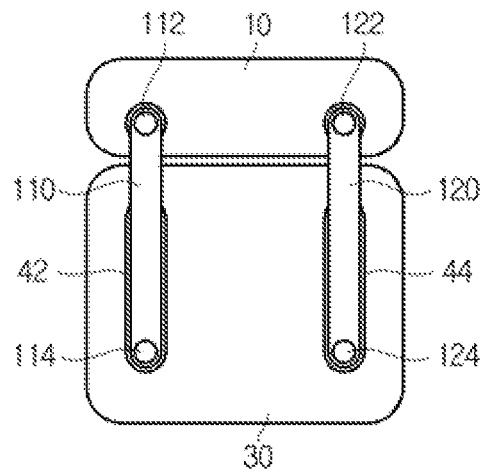
FIG. 5, FIG. 6 and FIG. 7 are drawings illustrating a operation status of the control panel of the ultrasonic diagnostic apparatus in accordance with another embodiment of the present disclosure.
Figure 5:
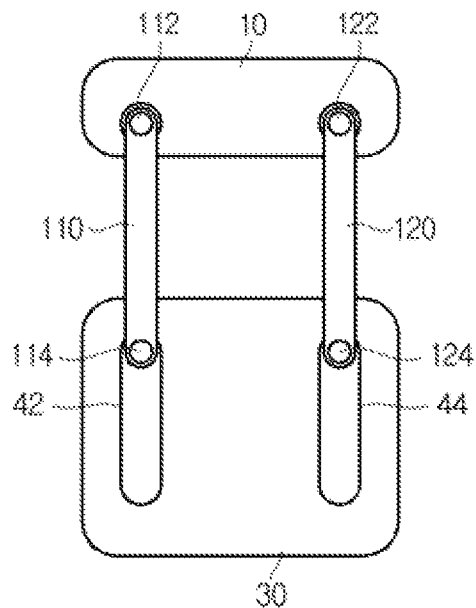
Figure 5:
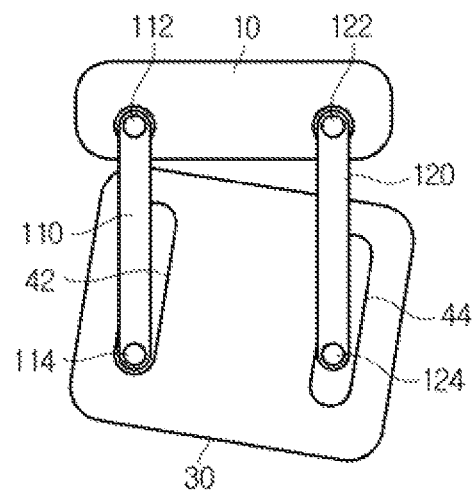
Figure 5:
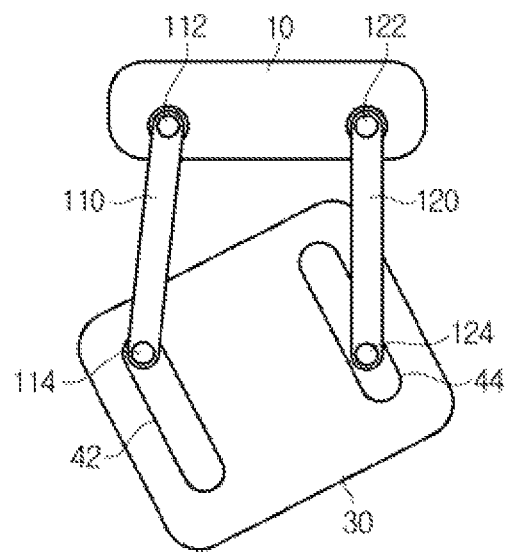
Figure 6:
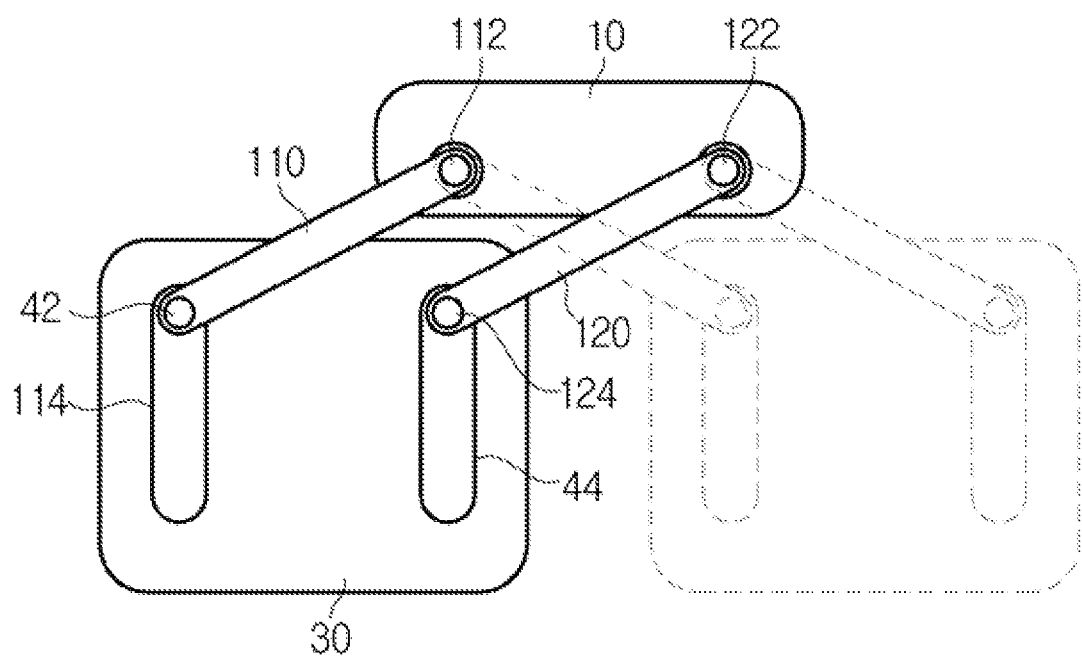
Figure 7:
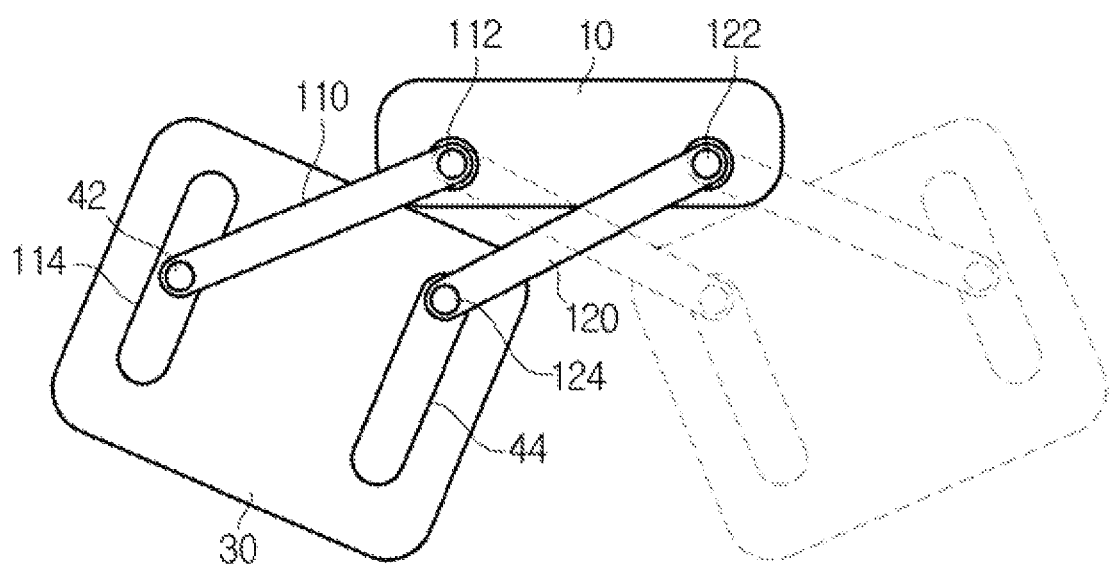

FIG. 5, FIG. 6 and FIG. 7 are drawings illustrating a operation status of the control panel of the ultrasonic diagnostic apparatus in accordance with another embodiment of the present disclosure.

As illustrated on FIG. 5 (a) and (b), the control panel 30 may be moved toward the forward/backward directions, that is, toward the x-axis and—x-axis directions, of the body 10. In addition, as illustrated on FIG. 5 (c), the control panel 30 may be rotated at a predetermined position. In addition, as illustrated on FIG. 5 (d), the control panel 30 may be rotated while moving toward the left side and right sides.

As described above, the motions as such may be overlappingly taken place. As illustrated on FIG. 6, the control panel 30 may be moved toward the left and right sides while in a state of being closely attached with respect to a front surface of the body 10. The control panel 30 in accordance with an embodiment of the present disclosure may only be moved toward the left and right sides without moving toward the unnecessary forward/backward directions.

As illustrated on FIG. 6, the control panel 30 that is moved toward all the way to the right side, that is, toward the y-axis direction, while in a state of being closely attached with respect to the front surface of the body 10 may be moved toward the left side, that is, toward the—y-axis direction. At this time, the control panel 30 may be closely attached with respect to the front surface of the body 10 continuously as the first end unit 114 of the first connecting member 110 and the second end unit 124 of the second connecting member 120 are moved along the first rail 42 and the second rail 44.

In addition, as illustrated on FIG. 7, the control panel 30 may be moved along the body 10. The control panel 30 may be moved in a state of one side thereof is closely attached to the body 10 while rotating at an edge unit of the body 10.

Figure 8:
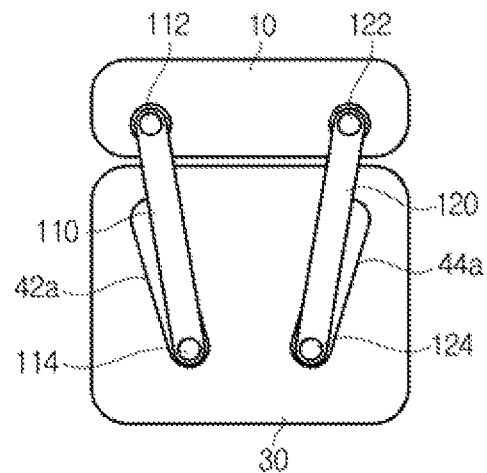
FIG. 8 is a drawing illustrating a operation status of a control panel of an ultrasonic diagnostic apparatus in accordance with still another embodiment of the present disclosure.
Figure 8:
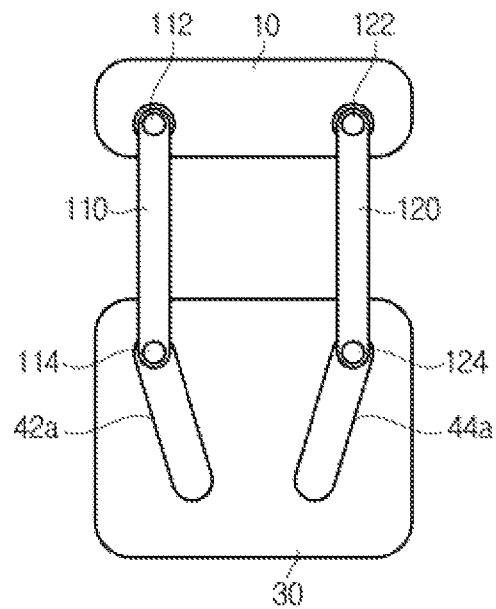
Figure 8:
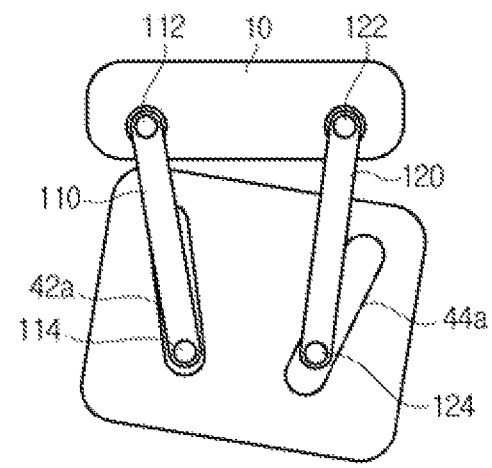
Figure 8:
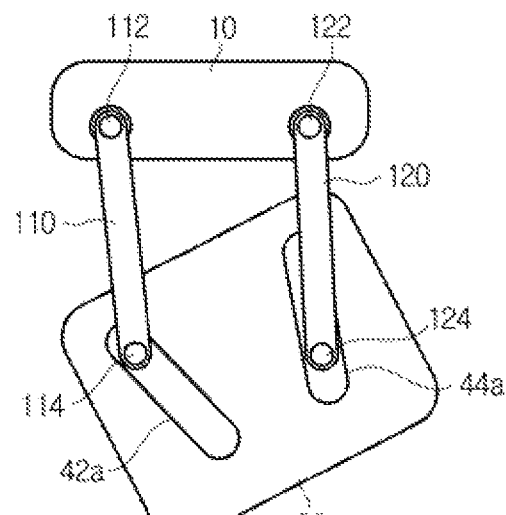

FIG. 8 is a drawing illustrating a operation status of a control panel of an ultrasonic diagnostic apparatus in accordance with still another embodiment of the present disclosure.

As illustrated on FIG. 8, a first rail 42a and a second rail 44a may be unparallelly disposed. As illustrated on FIG. 8 (a) and (b), the control panel 30 may be moved toward the forward/backward directions, that is, toward the x-axis and—x-axis directions, of the body 10, and as illustrated on FIG. 8 (c), the control panel 30 may be rotated at a predetermined direction. In addition, as illustrated on FIG. 8 (d), the control panel 30 may be rotated while moving toward the left and right sides. With the structure as such, the movements shown on FIG. 6 and FIG. 7 may be moved.

Figure 9:
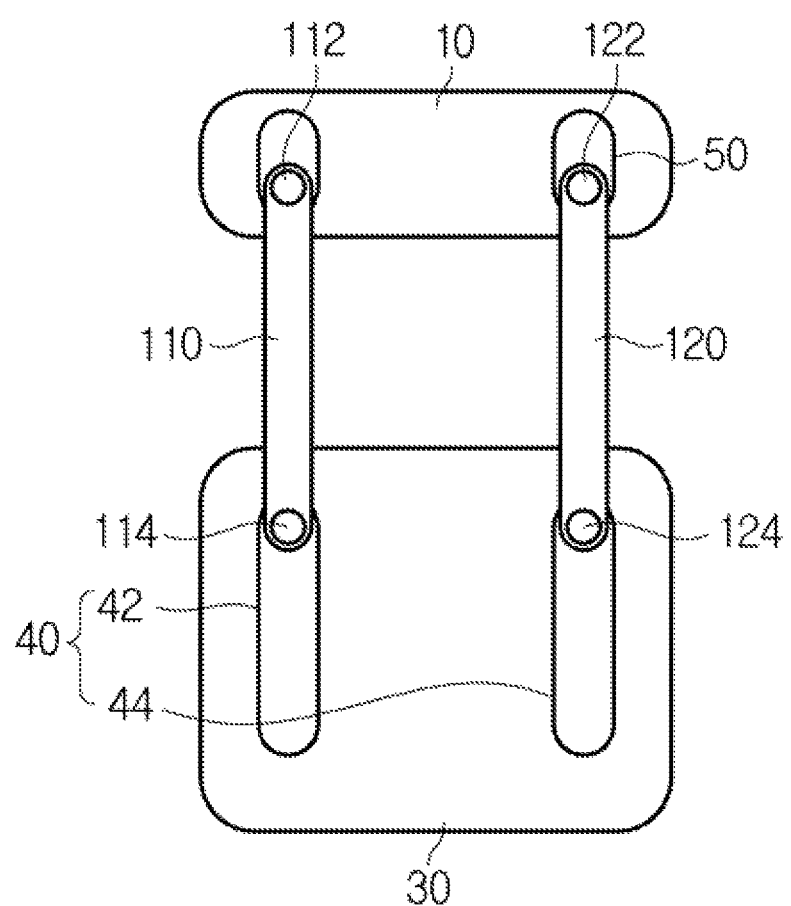
FIG. 9 is a drawing illustrating a rail structure of the ultrasonic diagnostic apparatus in accordance with another embodiment of the present disclosure.

FIG. 9 is a drawing illustrating a rail structure of the ultrasonic diagnostic apparatus in accordance with another embodiment of the present disclosure.

As illustrated on FIG. 9, the rail 40 and a rail 50 may be installed at the control panel 30 and the body 10, respectively. The rails 40 and 50 may include a body rail 50 installed at the body 10, and a moving rail 40 installed at the control panel 30. The first end units 112 and 122 may be moved along one surface of the body 10 by following the body rail 50, and the second end units 114 and 124 may be moved along one surface of the control panel 30 by following the moving rail 40.

On FIG. 9, the each of the body rail 50 and the moving rail 40 is parallelly disposed, but the body rail 50 and the moving rail 40 may not be parallelly disposed as well. In addition, the movements shown on FIGS. 5 to 8 may be taken place. Kin addition, the control panel 30 may be further moved toward a front of the body 10 as the body rail 50 is added, and the length of the first connecting member 110 and the second connecting member 120 may be reduced.

Figure 10:
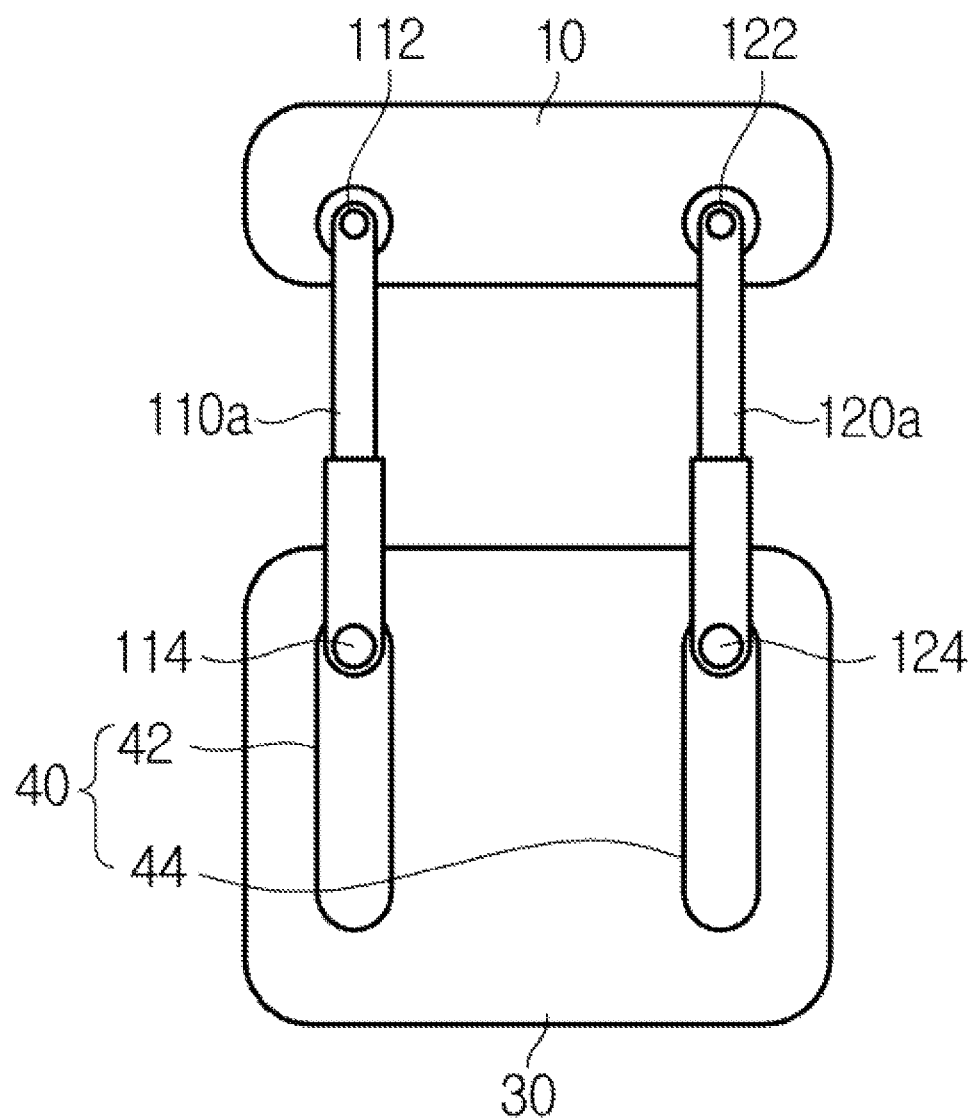
FIG. 10 is a drawing illustrating a connecting unit of the ultrasonic diagnostic apparatus in accordance with another embodiment of the present disclosure.

FIG. 10 is a drawing illustrating the connecting unit of the ultrasonic diagnostic apparatus in accordance with another embodiment of the present disclosure.

A first connecting member 110a and a second connecting member 120a may be provided in a plurality of levels. As illustrated on FIG. 10, as the first connecting member 110a and the second connecting member 120a may be provided in two levels. In addition, the first connecting member 110a and the second connecting member 120a may be provided in three levels.

Thus, the length of the each of the first connecting member 110a and the second connecting member 120a may be taken place. Accordingly, a user may be able to move the control panel 30 to a further large area.

Figure 11:
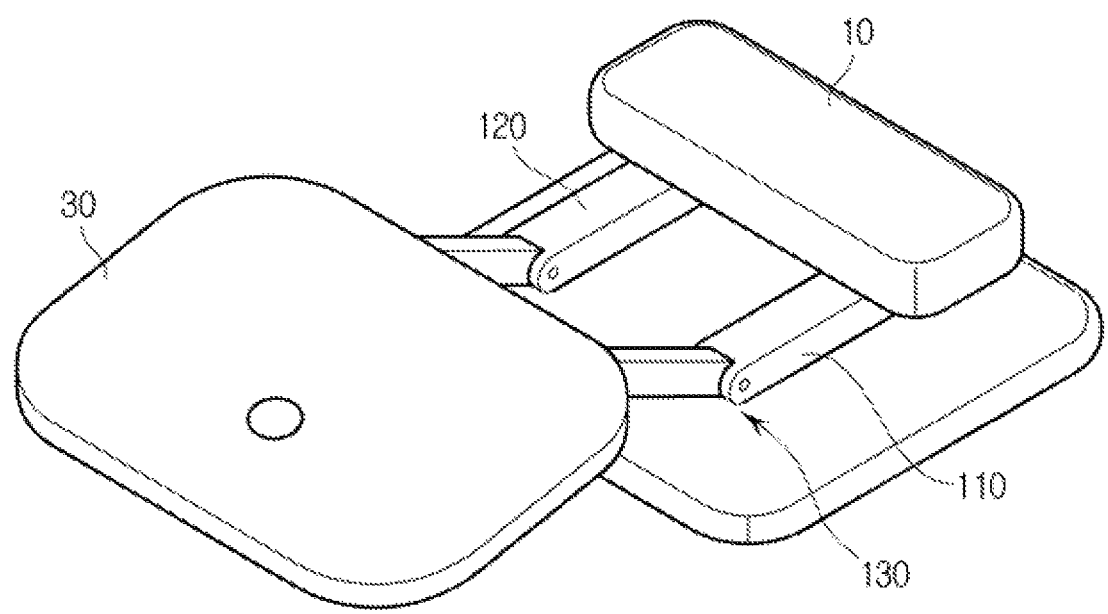
FIG. 11 is a drawing illustrating a connecting unit of an ultrasonic diagnostic apparatus in accordance with still another embodiment of the present disclosure.
Figure 12:
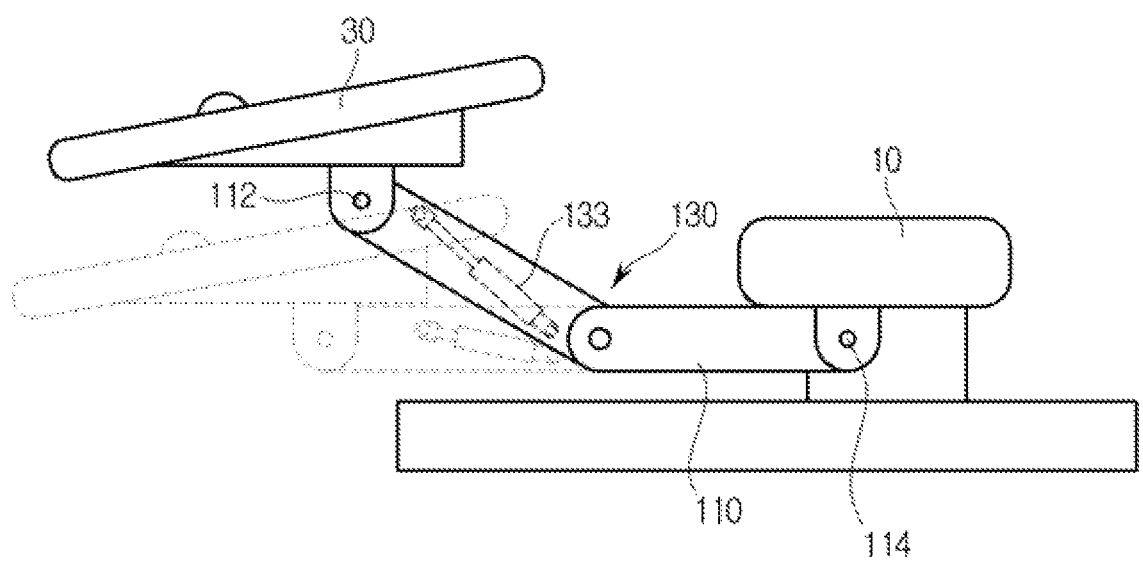
FIG. 12 is a drawing illustrating the connecting unit of FIG. 11 from a side.

FIG. 11 is a drawing illustrating the connecting unit of an ultrasonic diagnostic apparatus in accordance with still another embodiment of the present disclosure, and FIG. 12 is a drawing illustrating the connecting unit of FIG. 11 from a side.

The connecting unit 100 may include at least one folding unit 130 disposed in between the first end unit 112 and the second end unit 114. On FIG. 11 and FIG. 12, the one folding unit 130 is disposed at the first connecting member 110 and the second connecting member 120.

The folding unit 130 may be installed such that the second end unit 114 may be movably installed toward vertical directions with respect to the first end unit 112. That is, the control panel 30 may be moved toward vertical directions, that is, the z-axis and—z-axis directions, of the body by use of the folding unit 130. The control panel 30 may also be moved on the x-y plane surface, as well as toward the z-axis direction.

The connecting unit 100 may include a folding driving unit 133 configured to drive the folding unit 130. The folding driving unit 133 may be provided at inner sides of the first connecting member 110 and the second connecting member 120. The folding driving unit 133 may be formed by use of a gas spring. The height of the control panel 30 may be adjusted by installing a driving motor at one side of the gas spring and then by compressing and expanding the gas spring. In addition, the folding driving unit 133 may be provided in a structure having a link and a hinge.

That is, the control panel 30 may be moved to a random position on an x-y-z space. The control panel 30 may be moved from the first position to the second position according to needs of a user, and the first position and the second position are the random positions on the x-y-x space. The control panel 30 may be moved from the first position to the second position in last distance.

Figure 13:
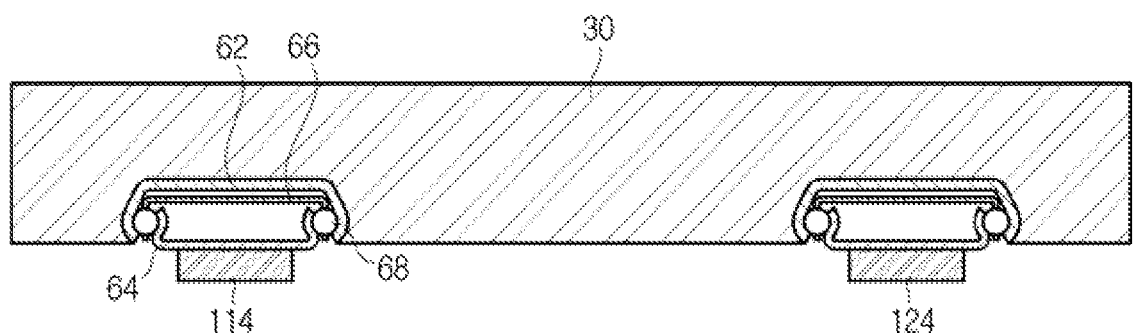
FIG. 13 is a drawing illustrating a rail of the ultrasonic diagnostic apparatus in accordance with one embodiment of the present disclosure.
Figure 14:
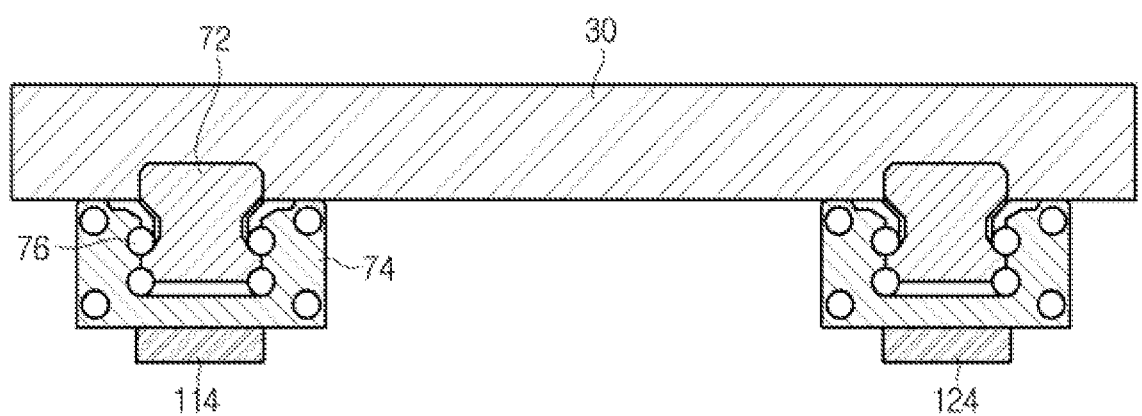
FIG. 14 is a drawing illustrating the rail of the ultrasonic diagnostic apparatus in accordance with another embodiment of the present disclosure.

On FIG. 13 and FIG. 14, various forms of a rail are illustrated. However, the various forms of the rail as such are provided as examples, and include all forms of the rotatably movable rails.

As described above, the rail may be integrally formed with the body 10 and the control panel 30. In addition, the rail may be provided in the form of a separate member as to be attached to the body 10 and the control panel 30. Hereinafter, the various forms of the rail formed at a lower surface of the control panel 30 will be described.

FIG. 13 is a drawing illustrating the rail of the ultrasonic diagnostic apparatus in accordance with one embodiment of the present disclosure. FIG. 13 is provided to illustrate an A-A' cross section on FIG. 4 as to describe the structure of the rail.

The rail may include member units 62 and 64, and a moving retainer 66 disposed in between the member units 62 and 64. The member units 62 and 64 may be provided in a plurality of units, and the moving retainer 66 as well accordingly be provided in a plurality of units. On FIG. 11, the two units of the member units 62 and 64 are illustrated, and the member unit includes an outside member 62 and an inside member 64.

The outside member 62 may be recessively provided at a lower surface of the control panel 30. In addition, the outside member 62 may be integrally formed with respect to a lower surface of the control panel 30. The inside member 64 may be insertedly disposed into the outside member 62. The moving retainer 66 having a ball bearing 68 may be disposed in between the outside member 62 and the inside member 64. The second end units 114 and 124 may be rotatably coupled at the inside member 64.

The inside member 64 may be slidingly and smoothly moved at the outside member 62 by use of the moving retainer 66. The second end units 114 and 124 coupled to the inside member 64 as well may be slidingly moved along the outside member 62. FIG. 14 is provided to illustrate the A-A' cross section on FIG. 4 as to describe the structure of the rail.

The rail may be provided in the form of a linear guide. The rail may include a guide rail 72, and a block 74 moving along the guide rail 72. An insertion retainer 76 may be disposed in between the guide rail 72 and the block 74.

The guide rail 72 may be protrudedly provided at a lower surface of the control panel 30. In addition, the guide rail 72 may be integrally formed with respect to a lower surface of the control panel 30. The block 74 may be coupled as to be moved along the guide rail 72. The second end units 114 and 124 may be rotatably coupled to the block 74.

The block 74 may be smoothly and slidingly moved along the guide rail 72. The second portions 114 and 124 coupled to the block 74 as well may be slidingly moved along the guide rail 72. Thus, the second portions 114 and 124 may be slidingly moved and rotated.

Figure 15:
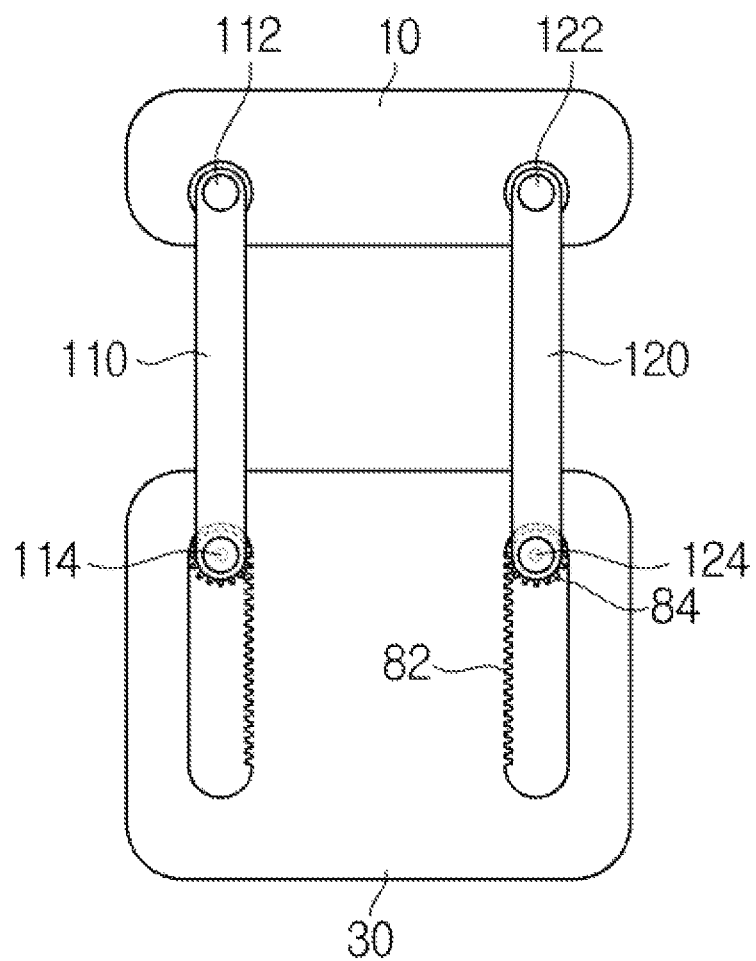
FIG. 15 is a drawing illustrating a rail of the ultrasonic diagnostic apparatus in accordance with still another embodiment of the present disclosure.

FIG. 15 is a drawing illustrating the rail of the ultrasonic diagnostic apparatus in accordance with still another embodiment of the present disclosure. On FIG. 15, a lower surface of the control panel is illustrated.

The rail may include a rack gear 82 and a pinion gear 84. The rack gear 82 may be provided at recessed one side of a lower surface of the control panel 30. The pinion gear 84 is provided as to correspond with respect to the rack gear 82, and may be disposed as to move along the rack gear 82. The second end units 114 and 124 may be coupled to the pinion gear 84 as to be independently rotated with respect to the pinion gear 84.

The pinion gear 84 may be moved along with the rack gear 82 while rotated. Accordingly, the second end units 114 and 124 coupled to the pinion gear 84 may be slidingly moved along the rack gear 82. Thus, the second end units 114 and 124 may be slidingly moved and rotated.

Figure 16:
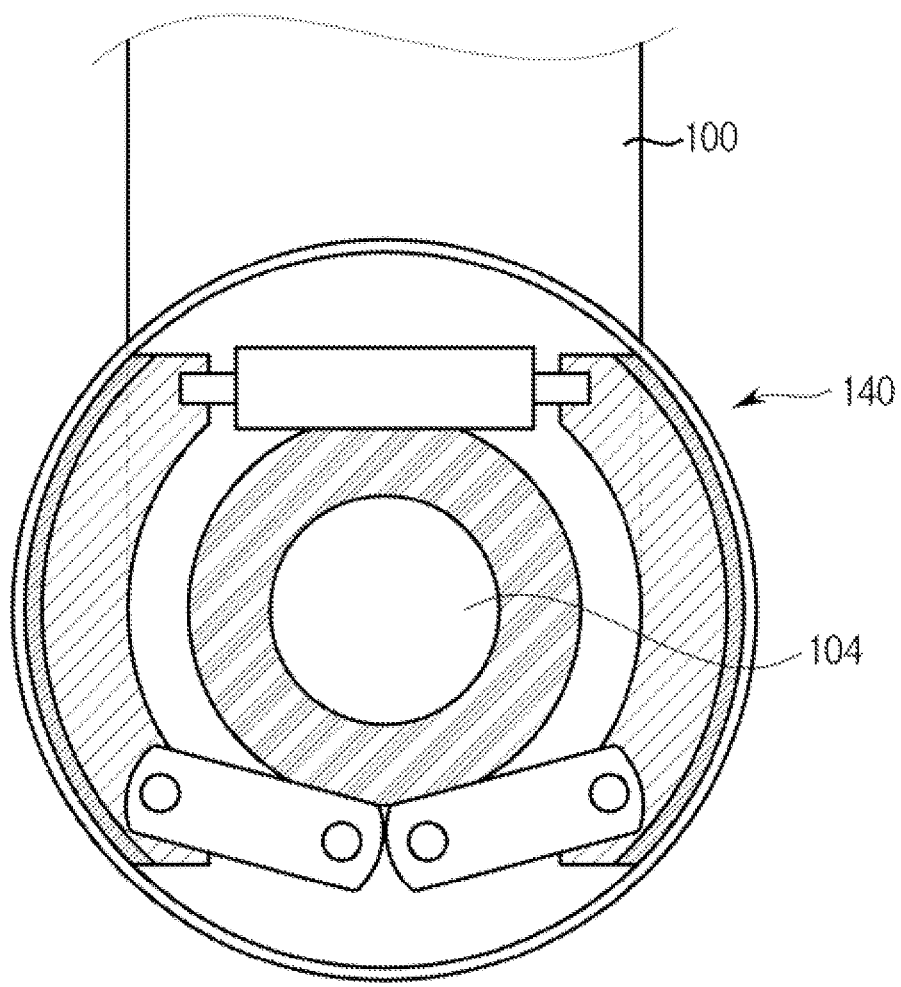
FIG. 16 is a drawing illustrating a fixing member of the ultrasonic diagnostic apparatus in accordance with one embodiment of the present disclosure.

FIG. 16 is a drawing illustrating a fixing member of the ultrasonic diagnostic apparatus in accordance with one embodiment of the present disclosure.

The connecting unit 100 may include a fixing member 140 to fix the first end unit 102 and the second end unit 104 at predetermined positions. In addition, the connecting unit 100 may include the fixing member 140 to fix the folding unit 130 at a predetermined position.

With respect to using the control panel 30 by a user, the control panel 30 may be moved to and fixed at a predetermined position. At this time, when the first end unit 102, the second end unit 104, and the folding unit 130 are moved by an outside force, a test may be interrupted. Thus, a fixing member as to fix the first end unit 102, the second end unit 104, and the folding unit 130 may be needed.

The fixing member 140 may be provided in various forms as to prevent rotations and sliding movements of the first end unit 102, the second end unit 104, and the folding unit 130. On FIG. 14, a case of when the fixing member 140 is provided in the form of a friction brake is illustrated, and the second end unit 104 installed at the control panel 30 is illustrated.

The friction brake may be disposed in a state of being spaced apart from an outer side of the second end unit 104. Accordingly, the second end unit 104 may be rotated at a predetermined position. The friction brake may be able to be moved in a state of being in contact with respect to the outer side of the second end unit 104 according to an input of the movement button 24 which is described earlier. Thus, the second end unit 104 may be prevented from being rotated.

In addition, the fixing member 140 may be provided in the form of a permanent magnet or an electromagnet. Depending on the input of electricity, the second end unit 104 may be provided in a state of being fixed at a predetermined position or in a state of being able to be moved. However, the above is provided as an example, and the fixing member 140 may include various forms of fixing the second end unit 104 at a predetermined position.

Figure 17:
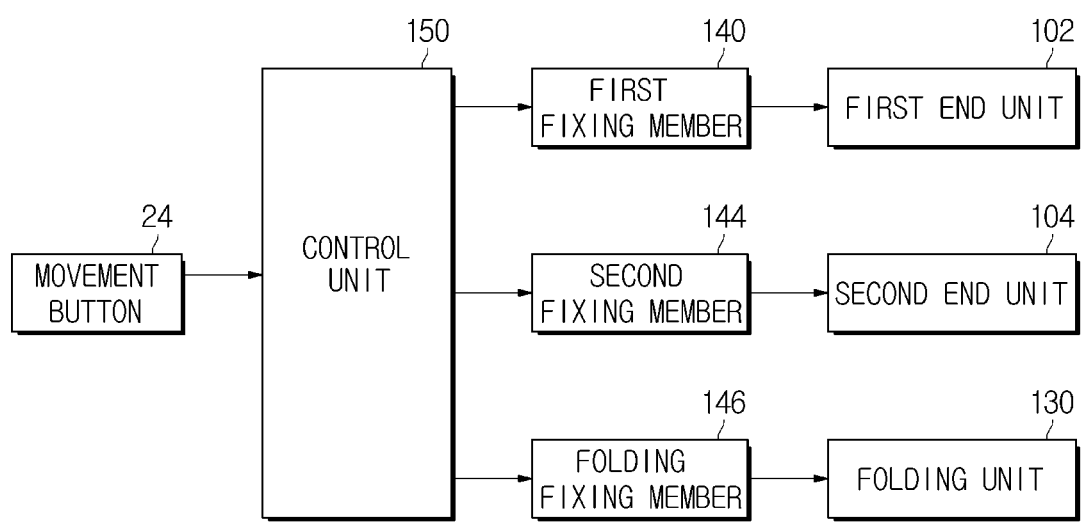
FIG. 17 is a drawing illustrating a flow control of the ultrasonic diagnostic apparatus in accordance with one embodiment of the present disclosure.

FIG. 17 is a drawing illustrating a flow control of the ultrasonic diagnostic apparatus in accordance with one embodiment of the present disclosure.

As described above, the ultrasonic diagnostic apparatus 1 may include the body 10, the control panel 30, and connecting unit 100 configured to connect the body 10 and the control panel 30. In addition, the connecting unit 100 may include the first end unit 102, the second end unit 104, the folding unit 130, and the fixing member 140. The fixing member 140 may include a first fixing member 142 to fix the first end unit 102, a second fixing member 144 to fix the second end unit 104, and a folding fixing member 146 to fixe the folding unit 130.

In addition, the ultrasonic diagnostic apparatus 1 may include a control unit 150 to control motions of the ultrasonic diagnostic apparatus 1. The control unit 150 may be able to control the first fixing member 142, the second fixing member 144, and the folding fixing member 146 according to the signals that are input from the movement button 24. Movements of the first end unit 102, the second end unit 104, and the folding unit 130 may be controlled according to the first fixing member 142, the second fixing member 144, and the folding fixing member 146.

FIG. 18 is a drawing illustrating a control method of the ultrasonic diagnostic apparatus in accordance with one embodiment of the present disclosure.

With respect to using the ultrasonic diagnostic apparatus by a user, the control panel 30 is generally used in a fixed state. Thus, a state of the movements of the first end unit 102, the second end unit 104, and the folding unit 130 being fixed is referred to as an initial state.

When the movement button 24 is input (160), the first fixing member 142 releases the fixing (162) of the first end unit 102 coupled to the body 10 as to be rotated and moved according to the command of the control unit 150. In addition, the second fixing member 144 releases the fixing (164) of the second end unit 104 coupled to the control panel 30 as to be rotated and moved. In addition, the folding fixing member 146 releases the fixing of the folding unit 130 as to be moved. At this time, the first fixing member 142, the second fixing member 144, and the folding fixing member 146 may be able to release the fixings of the first end unit 102, the second end unit 104, and the folding unit 130 simultaneously or in a random order.

Accordingly, the control panel 30 may be moved from the first position to the second position according to needs of a user (168). As described above, the first position and the second position may be random positions on the x-y plane surface, and the control panel 30 may be able to be moved from the first position to the second position in the least distance. In addition, the first position and the second position may be random positions on the x-y-x plane surface, and the control panel 30 may be able to be moved from the first position to the second position in the least distance.

The movement button 24 is input (170) as to fix the control panel 30 moved to the second position at the second position. Accordingly, the movements of the first end unit 102 disposed at a predetermined position is fixed by use of the first fixing member 142. In addition, the movements of the second end unit 104 are prevented as the second end unit 104 is fixed by use of the second fixing member 144. In addition, the movements of the folding unit 130 are prevented as the folding unit 130 is fixed by use of the folding fixing member 146. At this time, the first fixing member 142, the second fixing member 144, and the folding fixing member 146 may be able to fix the first end unit 102, the second end unit 104, and the folding unit 130 simultaneously or in a random order.

According to the ultrasonic diagnostic apparatus in accordance with the embodiments that are described so far, the control panel may be able to be moved to a desired position of a user, and thus the user convenience may be enhanced. In addition, space efficiency in utilizing the space may be enhanced as unnecessary movements to other positions such as forming a parabolic movement are not required.

From the above, the movements of the control panel, which is one example of the movement unit, are described. Other movement units, such as a display other than the control panel, as well may be able to be moved as such.

As is apparent from the above, a movement unit can be conveniently moved to a desired position by a user.

In addition, the movement unit can be fixed at a desired position or moved to a different position of a user according to needs of the user.

Although a few embodiments of the present disclosure have been shown and described, it would be appreciated by those skilled in the art that changes may be made in these embodiments without departing from the principles and spirit of the disclosure, the scope of which is defined in the claims and their equivalents.

What is claimed is:

1. An ultrasonic diagnostic apparatus, comprising:
   a body;
   a movement unit movably connected to the body and comprising at least one of a display or a control panel;
   a first connecting member and a second connecting member each having a first end unit rotatably coupled to the body so as to be rotatable in leftward and rightward directions of the body with maintaining coupled position of the first end unit and a second end unit of each of the first and second connecting members rotatably and slidably coupled to a first rail and a second rail respectively so as to be rotatable on the first rail and the second rail in the leftward and rightward directions of the body and movable on the first rail and the second rail in forward and backward directions of the body; and
   the first rail installed at the movement unit such that the second end unit of the first connecting member is movable in forward and backward directions of the body and rotatable in the leftward and rightward directions of the body, and the second rail installed at the movement unit such that the second end unit of the second connecting member is movable in the forward and backward directions of the body and rotatable in the leftward and rightward directions of the body,
   wherein when a distance the second end unit of the first connecting member slides along the first rail and a distance the second end unit of the second connecting member slides along the second rail are different from each other, an angle between the first connecting member and the first rail and an angle between the second connecting member and the second rail are different from each other.

2. The ultrasonic diagnostic apparatus of claim 1, wherein:
   the first rail and the second rail are installed on one surface of the movement unit such that the second end unit is moved along one surface of the body.

3. The ultrasonic diagnostic apparatus of claim 2, wherein:
   the second end unit of the first connecting member and the second end unit of the second connecting member are rotatably coupled to a lower surface of the movement unit, and the first rail and the second rail are installed at a lower surface of the movement unit.

4. The ultrasonic diagnostic apparatus of claim 3, wherein:
   the first rail and the second rail are recessively formed at a lower surface of the movement unit.

5. The ultrasonic diagnostic apparatus of claim 1, wherein:
   the first rail and the second rail comprise a body rail installed at the body, and a movement unit rail installed at the movement unit.

6. The ultrasonic diagnostic apparatus of claim 5, wherein:
   as for the first end unit of the first connecting member and the first end unit of the second connecting member to be moved along one surface of the body, the body rail is installed at the one surface of the body, and
   as for the second end unit of the first connecting member and the second end unit of the second connecting member to be moved along one surface of the movement unit, the movement unit rail is installed at the one surface of the movement unit.

7. The ultrasonic diagnostic apparatus of claim 1, wherein:
   the first rail and the second rail are installed on one surface of the movement unit while spaced apart from each other.

8. The ultrasonic diagnostic apparatus of claim 1, wherein:
   the first connecting member comprises at least one folding unit disposed between the first end unit and the second end unit of the first connecting member and the second connecting member comprises at least one folding unit disposed between the first end unit and the second end unit of the second connecting member.

9. The ultrasonic diagnostic apparatus of claim 8, wherein:

the second end unit of the first connecting member and the second end unit of the second connecting member are movable in upward and downward directions with respect to the first end unit of the first connecting member and the first end unit of the second connecting member, respectively.

10. The ultrasonic diagnostic apparatus of claim 1, wherein:
each of the first connecting member and the second connecting member comprises a fixing member configured to fix the first end unit and the second end unit at predetermined positions and comprises permanent magnet or an electromagnet.

11. The ultrasonic diagnostic apparatus of claim 1, wherein:
the movement unit comprises the control panel configured to control driving of the ultrasonic diagnostic apparatus.

12. The ultrasonic diagnostic apparatus of claim 1, wherein:
the movement unit comprises the display configured to display ultrasonic images.

* * * * *